United States Patent [19]

Rasor et al.

[11] E Re. 30,366

[45] Reissued Aug. 12, 1980

[54] ORGAN STIMULATOR

[75] Inventors: Ned S. Rasor, Sunnyvale, Calif.; Joseph W. Spickler, Lakewood, Colo.

[73] Assignee: Rasor Associates, Inc., Sunnyvale, Calif.

[21] Appl. No.: 723,635

[22] Filed: Sep. 15, 1976

Related U.S. Patent Documents

Reissue of:

[64] Patent No.: 3,835,864
Issued: Sep. 17, 1974
Appl. No.: 73,809
Filed: Sep. 21, 1970

[51] Int. Cl.[3] ..... A61N 1/36

[52] U.S. Cl. ..... 128/419 P; 128/785; 128/786

[58] Field of Search ..... 128/404, 418, 419 B, 128/419 E, 419 P, 419 PG, 419 PS, 2.06 E, 639, 642, 784, 785, 786

[56] References Cited

U.S. PATENT DOCUMENTS

| | | | |
|---|---|---|---|
| 3,087,486 | 4/1963 | Kilpatrick | 128/404 |
| 3,253,595 | 5/1966 | Murphy, Jr. et al. | 128/419 P |
| 3,367,339 | 2/1968 | Sessions | 128/419 P |
| 3,516,412 | 6/1970 | Ackerman | 128/418 |

FOREIGN PATENT DOCUMENTS

| | | | |
|---|---|---|---|
| 246004 | 11/1969 | U.S.S.R. | 128/419 P |

OTHER PUBLICATIONS

Hopps et al., "Surgery" vol. 36, No. 4, Oct. 1954, pp. 833-849.

Frei et al., "Medical Research Engineering", 4th Quarter, 1966, pp. 11-18.

*Primary Examiner*—William E. Kamm
*Attorney, Agent, or Firm*—Phillips, Moore, Weissenberger, Lempio & Majestic

[57] ABSTRACT

A stimulator device for insertion in a living body and having particular advantage for intra-cardiac use comprising a structure having a body form of a size and configuration to enable its transvenous or transarterial insertion, the surface of said body form providing electrode means for contact with a portion of the living body to be stimulated by said electrode means, and means mounted to project outwardly of and peripherally of said body form including anchor portions locating in a position displaced from said electrode means and providing means for engaging in portions of said living body to establish said electrode means in a required position of use, said electrode means having in connection therewith means to energize the same once said body form is located in its required position of use.

13 Claims, 15 Drawing Figures

ORGAN STIMULATOR

Matter enclosed in heavy brackets [ ] appears in the original patent but forms no part of this reissue specification; matter printed in italics indicates the additions made by reissue.

BACKGROUND OF THE INVENTION

Implanted Pacemaker devices are now commonly employed for the long-term treatment of atrioventricular (A-V) block. Such Pacemaker devices commonly employ flexible leads which connect a remotely positioned power pack with electrodes which are placed in contact with or attached to the myocardium. The techniques of implanting and using such Pacemakers, and many Pacemaker which have been used experimentally and in practice, are described by Siddons and Sowton, Cardiac Pacemakers (1967), published by Charles C. Thomas, Springfield, Illinois, Library of Congress Card No. 67-12042. Pacemakers having energy sources responsive to heart movement are shown in U.S. Pat. Nos. 3,358,690 and 3,486,506.

Such Pacemakers, or other biological stimulators working on these principles, have inherently suffered from certain disadvantages. The leads to the electrodes are commonly routed through veins leading into the heart itself. The movement of the heart and normal activity of the individual tend to put a strain on these leads and may result in lead breakage or dislodgement of the electrodes. The leads themselves, retained in situ, are frequently a source of irritation and infection. Further, since the electrical contact with the heart is made at the point or region of mechanical support or implantation, the normal fibrosis of tissue at these regions often results in a marked increase power required to pace, known as an increase in threshold. For example, the threshold has been found to increase on the order of ten times its original value until a plateau is reached over a period of two to three weeks. This requires a correspondingly greater power input to the electrodes, in the minimum of 3:1 over threshold, in order to achieve consistent pacing.

The remote power pack itself is a cause of discomfort and often a cause of difficulty. It is commonly implanted in a subcutaneous pocket beneath the pectoralis major or within the abdomen. Again, this provides a further opportunity for infection. Difficulty has been encountered in preventing migration of the power pack. Further, surgery is required from time to time to expose and replace the power pack due to exhaustion of the mercury cells. Prior pacing devices which derive their energy from the heart movement or pressures have commonly required thoracic surgery for attachment to the epicardium, and have employed flexible leads to the electrodes.

SUMMARY OF THE INVENTION

The present invention is directed to a wholly selfcontained stimulator which is particularly adapted for use as a Pacemaker. It is contained within a package or housing which is sufficiently small to be implanted by catheter insertion (transvenous or transarterial) into a chamber of the heart where it is attached to the endocardium. The stimulating electrodes are formed integrally with the unit, without external leads, and thus make contact with the endocardium. As used herein, "catheter" refers to an inserting device embodying a sheath-like element of small bore tube form.

A Pacemaker device made according to the present invention is intended primarily for long-term use. It can be used without discomfort to the user. The likelihood of a failure due to dislodgement of electrode contact, increase of threshold, or occurrence of infection is substantially reduced. Failure due to electrode lead breakage is eliminated entirely. The device can be implanted by a catheter device and technique which require only minor surgery and temporary discomfort to the patient. It can be recovered if desired or, if failure should occur it may simply be left in place and a new device inserted.

In one form of the invention a nucleonic battery is employed for providing a power source to the pulse generator circuits contained within the housing. This arrangement provides for an overall life which may be well beyond the normal life expectancy of the patient. For example, Pu-238 has a half life of 86 years, while Pm-147, which may be preferred because of lower costs, has a half life of 2.7 years. Suitable electronics in the converting and pulse generating portion are available which operate efficiently over three or more half lives. Operation over such a large power range is made possible in part by the fact that the device of the present invention does not cause a material or significant increase in threshold, and therefore can continue to operate after decay to very low power levels.

Three forms of the invention are disclosed which employ a biologically energized power source and thus derive their power requirements from the body itself. Prior attempts have obtained insufficient power from normal heart activity to provide reliable and continuous pacing. However, the apparatus of the present invention is one which does not result in a significant increase in threshold power and accordingly reliable pacing may be affected over an extended period of time with modest lower power requirements. The energy required for each stimulation pulse may be in the order of one microjoule or less, corresponding to a total power input to the electronics on the order of six microwatts or less. The mechanical work which is available substantially exceeds this.

In one form of the invention, a movable wall or diaphragm transforms hemodynamic pressure into electric energy by means of a suitable transducer. In other forms of the invention, a mass is suspended in such a manner that movements of the heart set up a sympathetic or harmonic movement of the mass, and this movement may be electromechanically coupled to produce energy. For example, the transducer may comprise a permanent magnet in combination with a non-moving electric coil. In another form, the mass may be connected to stress a piezoelectric crystal.

The body or housing structure of the present invention may also be used as the electrode structure for existing Pacemakers, as it offers certain advantages over the endocardial electrodes which are presently in use.

Another important object of the invention is the provision of a bioelectric stimulator which is fully selfcontained and implantable at the site of simulation, and an improved electrode structure therefor.

A further object of the invention is the provision of a stimulator, heart Pacemaker, or an electrode structure for a Pacemaker, in which the region of attachment is spaced from the region of stimulation to avoid the adverse effects of tissue fibrosis at the region of attachment.

A further object of the invention is a provision of a catheter for inserting the Pacemaker or electrode assembly therefor, as described above, and the further provision of the combination of a novel catheter and Pacemaker or electrode assembly therefor. The catheter is preferably a triaxial arrangement in which one of three concentric elements is removably secured to the body of the device, a second element forms a torque tube which may be used to assist in implanting the device and for removing the first element from the device, and the third element comprises an outer removable sheath which preferably extends at least partially over the body of the device during transvascular passage and may be employed to retain the body-attaching members on the device in a retracting or inoperative position until the device has been positioned, as desired. Thereafter, the sheath may be retracted to expose the body of tissue-attaching members, or extended to cover these members for removal of the device from the heart.

These and other objects and advantages of the invention will be apparent from the following description, the accompanying drawings and the appended claims.

DESCRIPTION OF PREFERRED EMBODIMENTS

Figure 1:
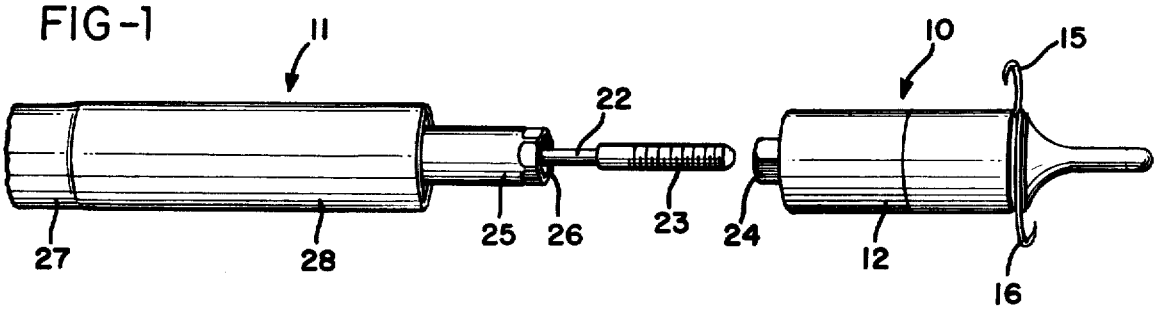
FIG. 1 is an exploded view of the stimulator and catheter devices of the invention.

Referring to FIGS. 1–4, a self-contained stimulator 10, particularly is adapted as a heart pacer, and a catheter 11 is adapted for use with such pacer. The pacer 10 is formed with an elongated capsule-like, generally cylindrical body 12. Preferably, the body 12 is formed exclusively on its outer surfaces of biologically compatable materials, the major portion of which may be stainless steel. While the outer surface of the body 12 is shown in the drawings as being formed essentially of smooth inert material, such as stainless steel, it is within the scope of this invention to provide the body with a compatible flocking material, such as a [dacron] *Dacron* weave to promote the formation of neointima once the unit has been implanted.

The device can be implanted in any of the four chambers of the heart where patho-physiology would be optimum for a particular patient. However, the preferred embodiment herein will emphasize implantation within the right ventricle where the greatest clinical and experimental experience has been concentrated to date. When the stimulator, or pacer 10, is adapted for implantation directly within a heart ventricle, it should have a maximum overall length not substantially exceeding 30 mm and preferably in the order of 18 mm or less. The diameter of the body 12 should not substantially exceed 10 mm and is preferably 8 mm or less. Such dimensions provide a self-contained Pacemaker which is sufficiently small to permit catheter transvascular insertion into a ventricle, and permit it to be received within such ventricle without disturbing the proper function of the heart.

Figure 4:
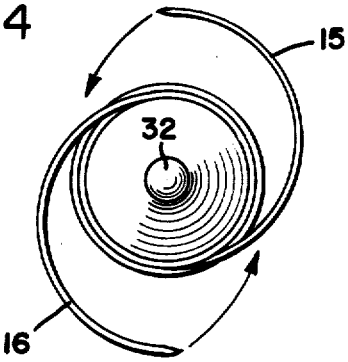
FIG. 4 is an end view of the device of FIG. 3.

The forward end of the body 12 is provided with means for attaching the pacer 10 to the myocardium. A preferred form of the attachment comprises a pair of oppositely directed spiral stainless steel attaching points or wires 15 and 16, as best shown in FIG. 4. The wires have inner ends attached to the circumference of the body 12 and free outer ends. These attaching wires are adapted to be retained in a retracted position in closely surrounding relation to the circumference of the body 12, but when released, spring out to the expanded or operative position, as shown.

Figure 2:
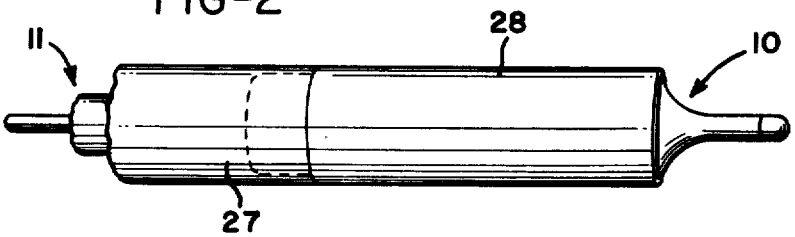
FIG. 2 shows parts of FIG. 1 in an assembled condition.
Figure 3:
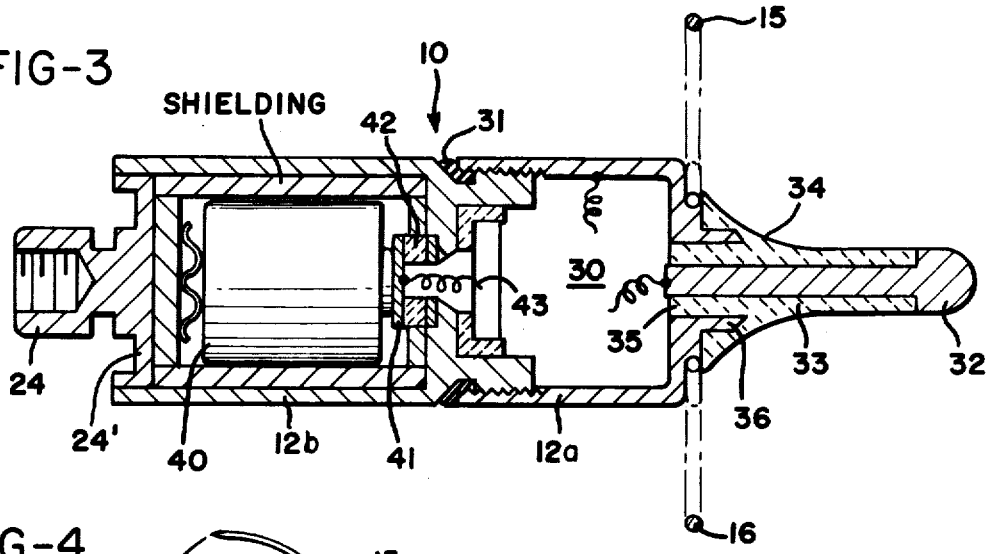
FIG. 3 is an enlarged sectional view, partially in diagrammatic form, of the stimulator of FIG. 1 adapted particularly for use as a heart pacer.

Catheter means for transvenous implanting of the Pacemaker 10 preferably consists of the triaxial device illustrated generally at 11 in FIGS. 1 and 2. This arrangement comprises a central rod 22 which is formed with a threaded end 23 which is adapted to be attached or received with a suitable internally threaded nut 24 formed on the rear wall 24' of the body 12, as shown in FIG. 3. A torque tube 25 is slidably received over the rod 22 and, at its forward end, is formed with an internal socket portion 26 adapted to be received over the nut 24 in driving engagement with the Pacemaker 10. The catheter is further provided with an axially slidable sheath 27 which has a forward metallic end portion 28 of a diameter sufficiently to be received at least partially over the body of the Pacemaker 10. In use, the sleeve 28 substantially covers the Pacemaker and retains the attaching wires 15 and 16 in their retracted position substantially as shown in FIG. 2. The use of the catheter 11 is further described in connection with the illustration of FIGS. 5a–c.

This entire catheter system may be rigid with defined bends or may be flexible or may be steerable. In the preferred form, a central rod 22 and the torque tube 25 are flexible, while the forward end of the sheath 27 is formed with a predetermined bend as indicated at 27' in FIG. 5a. The bend which may be formed within 2–4 inches of the end of the catheter assembly, may have an angle of approximately 30° in order to permit the catheter and the attached Pacemaker to be steerable around corners and bends.

Figure 6:
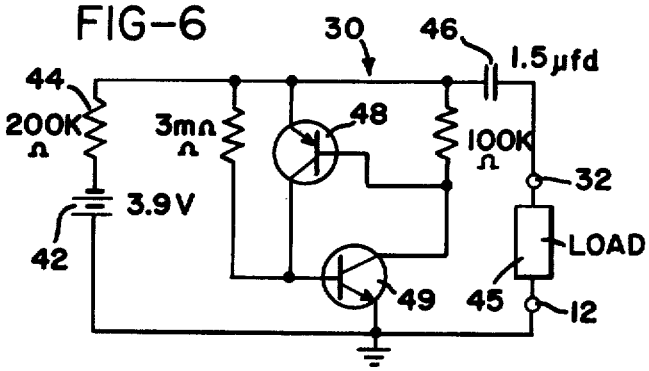
FIG. 6 is a schematic drawing showing a pulsing circuit which may be used with this invention.
Figure 7:
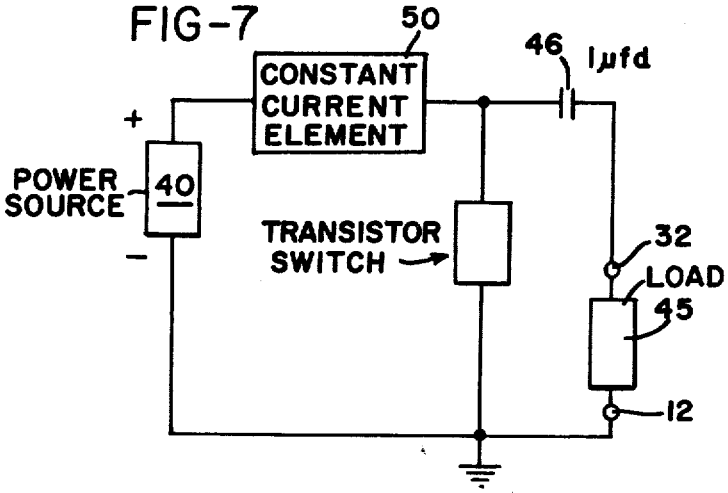
FIG. 7 is a diagram of a modified form of the circuit of FIG. 6 particularly adapted for use with a nucleonic or other varying power source.

Referring particularly to FIG. 3, the Pacemaker 10 is shown as including a forward body portion 12a and a cylindrically continuous rear body portion 12b. The forward portion 12a is hollow and contains the electronic pulsing circuit 30, illustrative examples of which are shown in FIGS. 6 and 7. It has been found that relatively simple circuits are totally satisfactory and are in fact preferred over the more complicated circuits shown, for example, in the reference text referred to under the Background section of the specification. The simpler circuits generally have lower losses and greater overall reliability. Such circuits can easily be fitted within the activity defined with the body section 12a without the necessity of reverting to microminiature or integrated circuits. However, such circuits permit even further miniaturization, but the overall size of the stimulator of this invention is dictated not so much by the circuit requirements but by the space requirements of the power source.

The body sections 12a and 12b may be threaded together and sealed as shown at 31, but it is within the scope of this invention to make the body 12 of simple one-piece construction. The rear wall 24' is preferred welded to the case 12b by electron beam welding. There is some advantage in the two-piece body construction of FIG. 3 in that it permits the body parts to be separated and adjustments to be made to the circuit prior to insertion.

One of the important advantages of the stimulator of the present invention resides in the fact that the pacing electrodes are formed integrally with outer surfaces of the body 12. To this end, the body portions 12a and 12b themselves define the positive pulsing electrode which, as previously noted, may be formed preferably of stainless steel. The negative pulsing electrode 32 is formed preferably of platinum and supported on a forwardly extending dielectric pedestal 33. The pedestal is preferably formed of an inert ceramic, defining a hollow coaxial insulator. The insulator 33 may thus have an outer curved surface 34 leading smoothly from the electrode end 32 and flaring outwardly at the body 12a to assist in guiding the device during insertion. A tubular portion 35 extends into the interior of the body 12a. The forward end of the body 12a is formed with an annular ledge 36 to provide support for the insulator and for the electrode 32.

The stimulating electrode 32 may also be of the differential current density type, known as the "Parsonnet Electrode" and described by George H. Myers and Victor Parsonnet in Engineering in the Heart and Blood Vessels. (1969) John Wiley & Sons, New York, N.Y.

The arrangement as shown has several important advantages. In the first place, it will be noted that, unlike prior devices, the electrodes do not themselves form or comprise the attaching devices. Rather, the pacing electrodes are well spaced axially from the barbs 15 and 16. Thus, once these electrodes have made reliable pacing contact with the heart tissue, they do not transmit the destructive forces of attachment and retention to this tissue, and they remain free of the adverse affects of fibrosis which invariably occurs at the regions of attachment or forcible retention. In devices where the electrodes themselves are directly attached or are forcibly retained by pressing against the tissue, an approximately 10 times increase in the threshold is not uncommon. This occurs over approximately a two to three week period subsequent to implanting and then reaches a plateau. Such a substantial increase in threshold requires a corresponding increase in power requirements simply to overcome the threshold and to effect reliable stimulation. The elimination of the cause of threshold rise permits reliable pacing with substantially lower power consumption.

Another important advantage of the construction of FIG. 3 is the total elimination of external flexible leads between the pacing circuit and the tissue to be stimulated. This then results in the elimination of the lead placement and breakage difficulties which are inherently associated with remotely positioned pacer circuit.

A further important advantage of the pacer of this invention is the fact that it can be reliably powered from a suitable nucleonic power source 40. There are available in the present state of the art a number of nucleonic conversion devices which may be contained within the physical dimensions of the body portion 12b, and suitably shielded and sealed therein. A preferred form of such device is a betavoltaic converter which is, in effect, a stack of semiconductor photocells which are coated with a radioactive material and which are irradiated by beta particles to produce an unidirectional current electric output. Beta sources may include Pm-147 which has a 2.7 years half life. It is within the state of the art to provide an electronic circuit which will operate effectively over more than three half-lives of such power sources within the volume available. The use of tritium, with a half life of 12.6 years, is also possible.

A power source 40 using radioisotope fuel may also be of the thermionic type, the thermoelectric type or the double conversion type. In the thermionic and thermoelectric types, heat from the radioisotopic fuel is transformed into electric power by electron transport through a thermionic diode or thermocouple respectively. In the double conversion type, radiation from the radiosotope fuel is employed to excite a light-emitting phosphor, and the photons in turn excite a semiconductor photocell. All three of these types can use Pu-238, which is a desirable fuel for biological applications and has a half life of 86 years. The choice of fuel and type of convertor will depend upon the cost of the source material and fabrication, the half life, and the efficiency of conversion as well as the shielding required. Suitable radioisotope-fueled batteries are made by Donald W. Douglas Laboratories, 2955 George Washington Way, Richland, Washington and sold under the tradenames "Betacel" and "Isomite," representing beta-voltaic and thermionic types respectively. While nucleonic power sources are preferred by reason of long life, it is within the scope of the invention to employ rechargeable batteries, or mercury cells. The latter may be satisfactory for short term pacing, in view of the relatively high overall efficiency of the device.

As shown in FIG. 3, an insulated plate 41 in contact with the power source is hermetically sealed by an insulator 42, and leads 43 extend to the circuit contained within the body section 12a. The case 12 is negative with respect to the power source but is positive with respect to the biological load.

The diagram of FIG. 6 illustrates one form of the pulsing circuit in which a power source 40 is shown as providing an output voltage of approximately 39 volts. This output is applied through charging resistor 44 and through the load 45 to a capacitor 46. The time required to charge the capacitor will depend upon the charging time constant of the circuit, and since the biological load 45 is normally less than 1,000 ohms it forms a small part of the total resistance in the charging circuit. However, as long as the load 45 is present the circuit will charge.

The transistors 48 and 49 comprise a transistor switch. This switch automatically becomes conductive to connect one side of the capacitor 46 to ground at some predetermined potential during the charging of the capacitor 46, and thus provides a low impedence grounding circuit permitting a discharge of the capacitor through the load 45. The peak load voltage may be 1.3 volts, and the transistor switch may be conductive for 3 ms. Thereafter, the current through the switching circuit drops to the point where it becomes nonconductive, and recharging of the capacitor 46 resumes through resistor 44, at a repetitive rate depending on the R-C constant.

It might also be noted that since the capacitor 46 is charged through the biological load a current reversal takes place between the negative pulsing electrode 32 and the case 12 which has the effect of reducing or eliminating polarization which otherwise occurs when electrodes are pulsed in the same direction in an electrolytic solution.

The diagram of FIG. 7 is essentially for the same circuit as shown in FIG. 6 except for the addition of a constant current element 50 which may comprise a constant current transistor. This circuit is useful to maintain a constant pulse height and rate when the pulsing circuit is used with nucleonic power source whose output decays with time, or with biologically activated power sources whose output varies with the amount of biological activity.

Figure 5A:
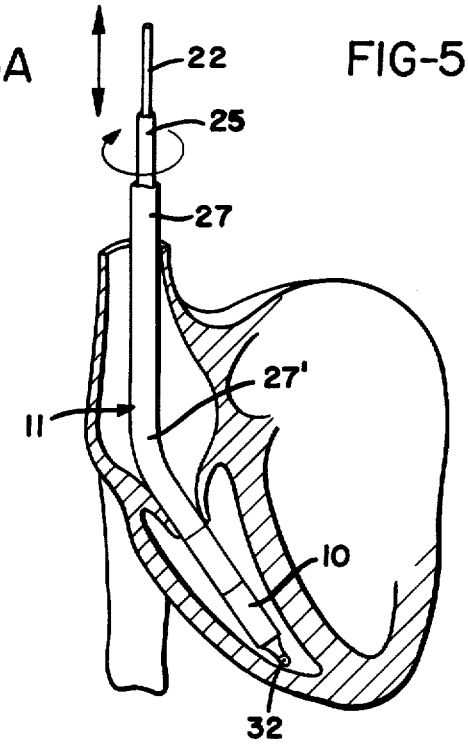
FIGS. 5a, 5b and 5c are, respectively, diagrams illustrating the method of implanting the pacer using the catheter device of this invention.

The method of implanting the Pacemaker of the present invention using the improved catheter is illustrated diagrammatically in FIG. 5. The Pacemaker is assembled with the catheter 11 as shown in FIG. 2. The catheter is formed with a fixed or predetermined bend 27' about two to three inches from the end, of about 20°–40° to enable it to turn corners while it is being inserted. The insertion technique itself is essentially the same as currently in use for the transvenous implantation of endocardiac electrodes and other cardiac catherization procedures. The Pacemaker may, for instance, be inserted in the right external jugular vein and advanced through the superior vena cava and through the right atrium into the apex of the right ventricular cavity. This is the position illustrated in FIG. 5a. This is accomplished, of course, under fluoroscopic observation.

Prior to attaching the Pacemaker, the effectiveness of its resting position may first be observed with an electrocardiograph to assure that it is functioning normally and that it has captured the heart. The end 28 of the sheath 27 is preferably made of conductive material, such as stainless steel, so that the electrode formed on the body 12 will conduct through the sheath.

Figure 5B:
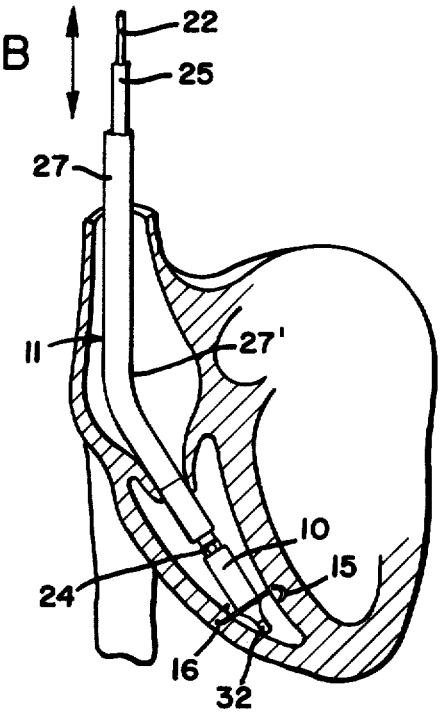

Having determined a proper position, the sheath may be partially retracted as shown in FIG. 5b to expose the barbs, and the torque tube 25 rotated clockwise to imbed the barbs in the myocardium. The entire Pacemaker, in this condition, will be wedged into the trabeculae making contact both with the case and with the tip electrode 32.

Figure 5C:
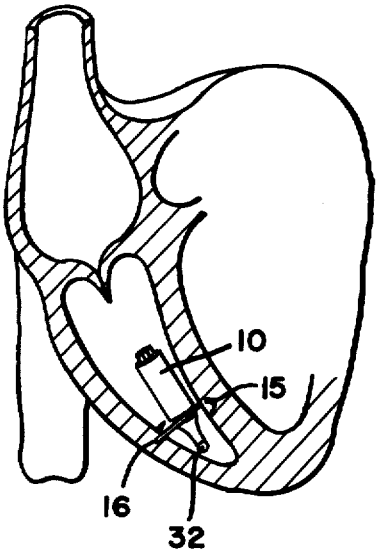

Once attachment in this manner is made, the torque tube 25 may be held against rotation and the rod 23 unscrewed from the internal threads in the nut 24. The entire catheter may then be extracted leaving the Pacemaker imbedded essentially as shown in FIG. 5c. The Pacemaker can be extracted from the heart by reversing the foregoing procedure.

The invention is not limited to heart pacing as such. Other examples of the direct implantation of the self-contained stimulator at the site of the stimulation without separate electrical leads include baropacing (stimulation of the baroreceptors in the neck or aortic arch), stimulation of the diaphragm for breathing (stimulation of the phrenic nerve), stimulation of the numerous sphincter muscles which control the flow of various body fluids and solids (at the sphincter site), and other such functions which have been shown to respond to electrical stimulation and which small size and absence of electrical leads would render feasible or more practical. In most such cases the self-contained stimulator described in FIG. 3 would deliver a pulse approximately every 20 milliseconds during activation of the biological function instead of about one pulse per second as in the cardiac Pacemaker. Activation of the pulse train could be accomplished by external command via an electromagnetic or magnetic signal from outside the body.

Figure 8:
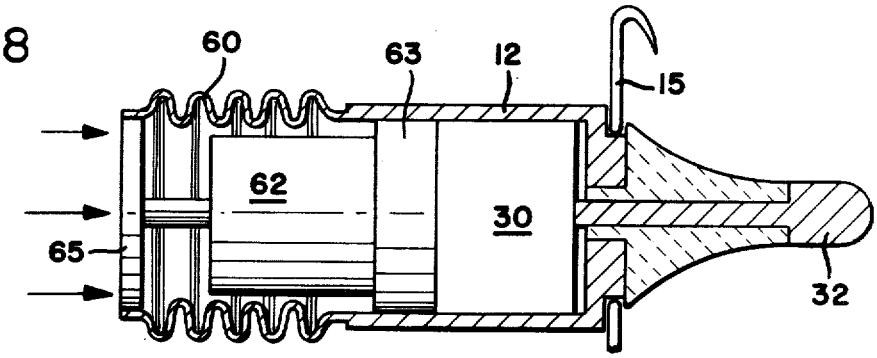
FIG. 8 shows a modified form of the invention adapted to respond to hemodynamic pressure changes.

The invention is not limited to an arrangement which contains as internal source of power. In FIG. 8 there is illustrated an embodiment of the invention which is responsive to hemodynamic pressure. The body section 12b is replaced by a flexible or movable section which incorporates a rubber diaphragm or metal bellows 60 which moves under the influence of pressure changes within the heart cavity. Forces and motions arising from such pressure changes are applied to an electromechanical transducer 62 the output of which may be applied to a suitable energy storing circuit 63. The transducer may be of the magnetic induction type or may be a piezoelectric generator. The storage device 63 may be a diode-isolated full-wave rectifier with capacitor storage. The energy thus stored is available for subsequent release to the stimulation electrodes by a pulse forming circuit substantially as previously described. The storage device will be kept charged by the succession of heart beats and therefore serves the function of the power source previously described.

For example, if the effective area of the movable section 65 is about ½ $cm^2$, and moves 1 mm under the influence of a 20 torr average pressure pulse, each beat would produce about 130 microjoules of mechanical work. Since less than 10 microjoules of electric energy is required for each pulse, a large margin of reserve power is available.

Figure 9:
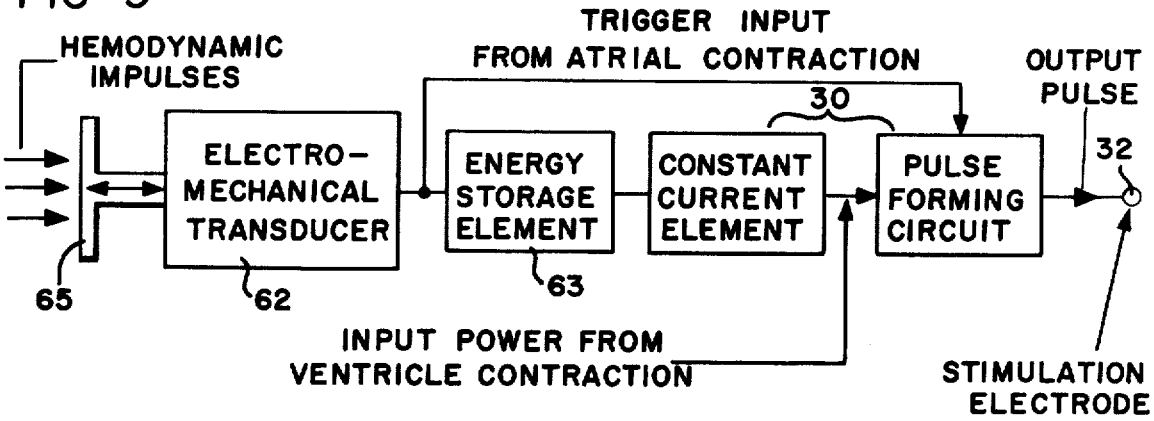
FIG. 9 is a block diagram of the pacer of FIG. 8.

A circuit diagram at FIG. 9 shows an arrangement of the pacer of FIG. 8 adapted as a synchronous pacer, to obtain the benefits from synchronous pacing by slaving the unit to the atriol systole. After storing the large power pulse generated by the transducer during the ventricular contraction, the pulse-forming circuit is "armed;" i.e. it reaches a condition in which the next significant electrical signal from the transducer will cause the circuit to "fire" and deliver an electrical pulse to the stimulating electrodes. Therefore, the pressure impulse from the next atrial contraction is transmitted through the tricuspid valve to generate an electrical signal from the transducer which fires the circuit. The stimulated ventricular contractions thereby become synchronized with the atrial contractions. It may be desirable to construct the circuit so that "arming" is delayed until after the refractory period of the heartbeat to avoid premature firing by reverberations from the ventricular construction. Also it may be desirable physiologically to provide a delay between the signal from the atrial contraction and the Pacemaker output pulse, similar to the delay in the A-V node.

Figure 10:
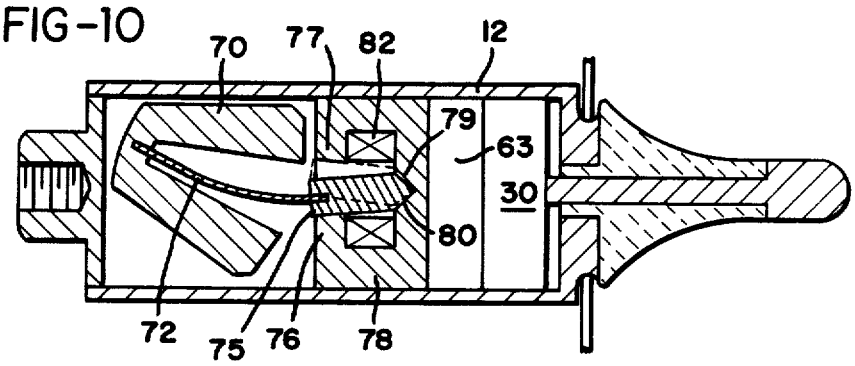
FIG. 10 is a further modification showing a biologically powered pacer according to the present invention.
Figure 11:
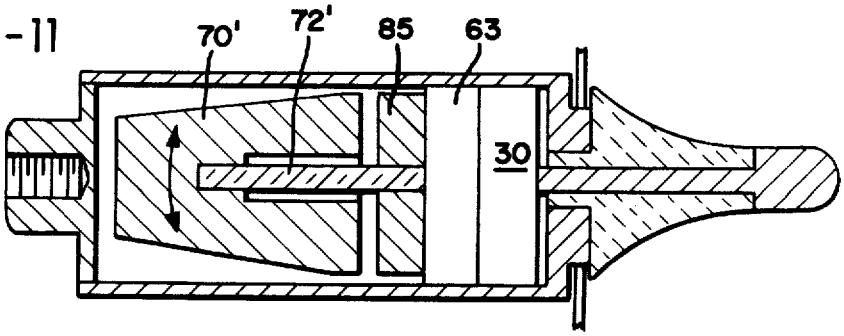
FIG. 11 is a still further modification showing another form of the biologically powered pacer.

FIGS. 10 and 11 illustrate additional arrangements by means of which the heart movement itself can be used to provide a suitable source of energy. Observation has shown that an implanted Pacemaker undergoes transient displcements of about 1 cm within a 24th of a second. Assuming constant acceleration, a 5 mm displacement relative to the capsule over 1/24th second of an armature weight 4 grams would produce a force of about 2500 dynes acting over this distance, to produce about 120 microjoules of work per beat, again substantially in excess of the requirements of the Pacemaker. Referring to FIG. 10, a mass 70 is mounted in the manner of a pendulum on the end of a leaf spring 72. The natural oscillation rate of the mass 70 on the spring 72 may be that of the paced heart rate. The lower end of the spring 72 is joint with a magnetic armature 75 received between the poles 76 and 77 of a permanent magnet 78.

The lower end of the armature is retained in a V-shaped recess 79 by the magnetic attraction and is correspondingly formed with a knife or V-edge 80 to provide a pivotal movement. The poles 76 and 77 are spaced apart so that the armature 75 can assume either one of two stable positions, as shown by the full lines and broken lines. In one position, the flux is induced through the armature in one direction while in the other position it is induced in the opposite direction.

Since the pendulum formed by the mass 70 and spring 72 oscillates in resonance with the sinus rate of the heart, the bending moment of the spring 72 lifts the armature 75 from one pole face whereupon it abruptly moves to the opposite pole face, resulting in a sudden reversal of the flux and inducing an electric current in the surrounding coil 82. The coil output may be applied to the storage device 63, as described in connection with FIG. 8. FIG. 11 is similar to FIG. 10 except that the mass 70' and spring 72' are connected to stress a piezoelectric crystals 85. In this embodiment, the periodic rate of the mass and spring may be substantially greater than that of the heart, to produce a "ringing" effect with each beat.

Figure 12:
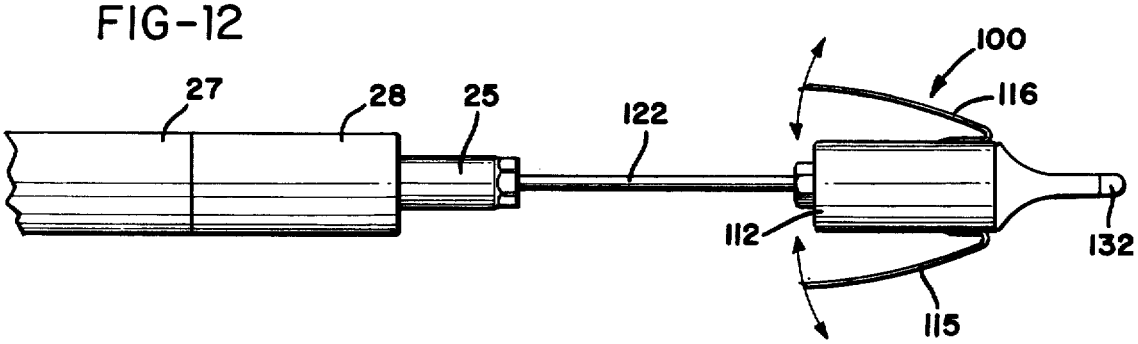
FIG. 12 is a modified catheter and an improved Pacemaker electrode assembly according to the teachings of this invention.

Certain of the teachings and advantages of the present invention may be used to improve the performance of existing pacemakers which presently use endocardinal electrodes. The body Pacemaker 10 may be modified for this purpose to perform the function of the electrodes only and an arrangement for this purpose is illustrated at 100 in FIG. 12. In this case, the cartridge body 112 is made similarly to the body 12 except that it does not contain any pulsing circuitry or power source, but merely comprises means for making electrical contact. Thus, the body 112 may conveniently be made to a smaller length and/or diameter than that which has previously been described. The outer surface of the body 112 thus comprises one of the electrodes, while stimulating electrode 132 may be made and supported on a ceramic pedestal spaced from the body 112 in the manner which has been described in connection with the electrode 32 of FIG. 3.

The electrode assembly 100 will be connected by flexible leads to a conventional remote pacer by means of a flexible electrical conduit or lead 122. The lead 122 may be a coaxial conductive cable, which has one of its leads connected to the case or body 112 and the other connected to the electrode 132. The assembly 100 may be used with remote pacers which employ a single electrode lead or a pair of leads. Where a single lead is used, it would be connected inside the body 112 to the electrode 132.

The electrode assembly of this invention is provided with a somewhat modified form of attachment comprising a pair of generally axially extending retaining wires 115 and 116. The forward ends of the wires are attached or secured to the body 12. The wires extend rearwardly and outwardly, and are movable between a retracted position in which the wires lie adjacent to the outer surface of the body, to a spread apart position, substantially as shown.

The general technique of inserting and implanting the electrode assembly 100 does not differ substantially from that described in connection with the pacemaker 10. The torque tube 25 and the sheath 27 may be used, with the rod 22 removed. The cylindrical conductive end 28 would be received partially over the body 112 with the attaching wires 115 and 116 collapsed and retained within end 28. The electrical lead 122 is threaded through the hollow torque tube 25.

It would be expected that the electrode assembly would be inserted well into the apex of the ventricle cavity accompanied by some stretching of the heart muscle. The torque tube 25 could be employed to provide axial forces as well as rotational alignment. The sheath 27 would then be retracted exposing the ends of the attachment wires 115 and 116, and when the axial force is released the ends of the wires would tend to imbed themselves within the heart muscle. If necessary, some pull could be placed on the lead 122 to complete the attachment, and then the catheter may be extracted leaving the electrode assembly 100 in place.

The electrode assembly 100 provides to a remote Pacemaker certain of the advantages of the present invention. Principally, the electrodes, which are formed as integral and discrete surface portions of the assembly, are not prone to dislodgement, movement, penetration or breakage. Further, they define regions of stimulation which are spaced from the region of attachment, as in the case of the Pacemaker 10, and thus remain free of the adverse affects of fibrosis.

It is accordingly seen that this invention provides a novel self-contained biological stimulator, which is particularly adapted for use as a Pacemaker, and an electrode assembly useful with existing Pacemakers. It is intended for long-term treatment of partial or complete A-V block. Synchronous pacing may be used, as desired, and the circuit can be modified as known in the art for demand pacing. For synchronous pacing of devices of the types of FIGS. 3, 10 or 11, a short sensing or trigger electrode wire may extend axially from the rear wall 24' of the body 12b through the tricuspid valve into the right atrium to pick up the atrium pulse as a control signal for the circuit 30. For demand pacing, the surface electrode 32 may be used to pick up the ventricle pulse and suppress the trigger circuit in the manner taught for example by Keller U.S. Pat. No. 3,431,912 or Greatbatch U.S. Pat. No. 3,478,746. The physical size of the capsules which form the bodies is sufficiently small to permit long-term treatment, such as in the case of a child. The apparatus and method of the attachment and implanting is one which results in minimum discomfort to the patient. In the event of failure, the size of the Pacemaker is sufficiently small to make is feasible to simply leave it in place and to insert a new one, although intervenous removal by catheter also is possible.

While the forms of apparatus herein described constitute preferred embodiments of the invention, it is to be understood that the invention is not limited to these precise forms of apparatus, and that changes may be made therein without departing from the scope of the invention.

What is claimed is:

1. A stimulator device for insertion in a living body and having particular advantage for intracardiac use comprising a structure having a body form for transvenous or transarterial insertion, electrode means on the surface of said body form for contact with a portion of the living body to be stimulated by said electrode means, and means mounted to project outwardly of and peripherally of said body form including anchor portions locating in a position displaced from said electrode means and providing means for engaging in portions of said living body to establish said electrode means in a required position of use, said electrode means having in connection therewith means to energize the same once said body form is located in its required position of use.

2. A stimulator device as in claim 1 wherein said means to energize said electrode means includes a power source positioning in a location remote from said body form.

3. A stimulator device as in claim 1 wherein said means to energize said electrode means includes a power source embodied within said body form.

4. A stimulator device as in claim 1 wherein spaced surface portions of said body form define separate electrode means.

5. A structure as in claim 1 wherein said anchor portions are defined by wire like segments connected with and biased to normally project outwardly from said body form to facilitate the establishment of a connection thereof with said living body in an area displaced from said electrode means.

6. A stimulator device as in claim 1 wherein said electrode means have a fixed positioning in respect to said body form and comprise at least two electrodes, and said body form includes insulator means separating said electrodes.

7. A stimulator device as in claim 1 characterized by said body form being a unitized structure having means for guiding the same for transvenous or transarterial insertion.

*8. A stimulator device for insertion against a portion of a living body, comprising:*

*a structure having a body form;*

*electrode means supported by said body form for non-attaching contact with a portion of the living body to be stimulated thereby; and*

*anchor means proceeding from said body form, said anchor means including anchor portions for location in a position in said living body, said anchor portions providing means for piercing and thereby engaging in said position of said living body, said anchor means including means for mounting said anchor portions to project outwardly of said body form and away from all portions of said electrode means for preventing formation of significant nonexcitable tissue such as fibrotic tissue adjacent to said electrode means due to irritation of said living body caused by said anchor means to establish said electrode means in a required position of use, said electrode means having in connection therewith means to energize the same one said body form is located in its required position of use.*

*9. A stimulator device is in claim 8, wherein in use said structure, electrode means and anchor means fit against a single side of an organ of said living body.*

*10. A stimulator device as in claim 9, wherein said organ comprises a heart.*

*11. A stimulator device for insertion in a living body, comprising:*

*a structure having a body form;*

*electrode means supported by said body form for non-attaching contact with a first surface of an organ in a living body, which organ is to be stimulated by said electrode means; and*

*anchor means, said anchor means including anchor portions locating in a position in said first surface of said organ, said portions providing means for engaging in said first surface of said organ, said anchor means including means for mounting said anchor portions to project outwardly of and displaced from all portions of said electrode means a distance sufficient to prevent significant formation of non-excitable tissue such as fibrotic tissue adjacent to said electrode means due to said anchor means to establish said electrode means in a required position of use, said electrode means having in connection therewith means to energize the same once said body form is located in its required position of use.*

*12. A stimulator device as in claim 11, wherein in use said structure, electrode means and anchor means fit generally against said first surface of said organ without passing piercingly through said organ from said first to a second surface thereof.*

*13. A stimulator device as in claim 12, wherein said organ comprises a heart.*

* * * * *